United States Patent [19]

Birang et al.

[11] Patent Number: 5,212,537

[45] Date of Patent: May 18, 1993

[54] CALIBRATION TECHNIQUE FOR MONOCHROMATORS AND SPECTROPHOTOMETERS

[75] Inventors: Monoocher Birang, Los Gatos; Kien Chuc; Ronnie Northrup, both of San Jose; Bruno Strul, Palo Alto, all of Calif.

[73] Assignee: Applied Materials, Inc., Santa Clara, Calif.

[21] Appl. No.: 551,349

[22] Filed: Jul. 12, 1990

[51] Int. Cl.$^5$ ............................................. G01J 3/00
[52] U.S. Cl. ..................... 356/300; 356/319; 356/328; 356/334
[58] Field of Search ............... 356/300, 319, 417, 243, 356/331–334, 326, 328

[56] References Cited

U.S. PATENT DOCUMENTS

| | | | |
|---|---|---|---|
| 3,645,627 | 2/1972 | Brody et al. | 356/243 |
| 4,198,120 | 4/1980 | Norris et al. | 356/328 |
| 4,660,974 | 4/1987 | Mächler et al. | 356/328 |
| 4,661,711 | 4/1987 | Harjunmaa | 356/417 |
| 4,669,873 | 6/1987 | Wirz | 356/328 |
| 4,758,085 | 7/1988 | Lequime et al. | 356/328 |
| 4,932,779 | 6/1990 | Keane | 356/319 |

OTHER PUBLICATIONS

Marques et al., "Fiber Optics Link to a Solar Spectrophotometer," Rev. Sci. Instrum. vol. 52 #3, Mar. 1981.
"Large Lamp Application Bulletin," Atlantic Ultraviolet Corporation, pp. 14–17.

Primary Examiner—F. L. Evans
Assistant Examiner—K. P. Hantis
Attorney, Agent, or Firm—John A. Frazzini

[57] ABSTRACT

A photometer having a plurality of input fibers to its optical entrance, at least one of which is for transmission of calibration light and at least one of which is for transmission of sample light. The exit ends of these fibers are aligned into a linear array, thereby producing an effective entrance slit for the optical entrance of the photometer. The fiber(s) for calibration light are positioned at the center of the linear array to avoid miscalibration due to photometer astigmatism.

6 Claims, 6 Drawing Sheets

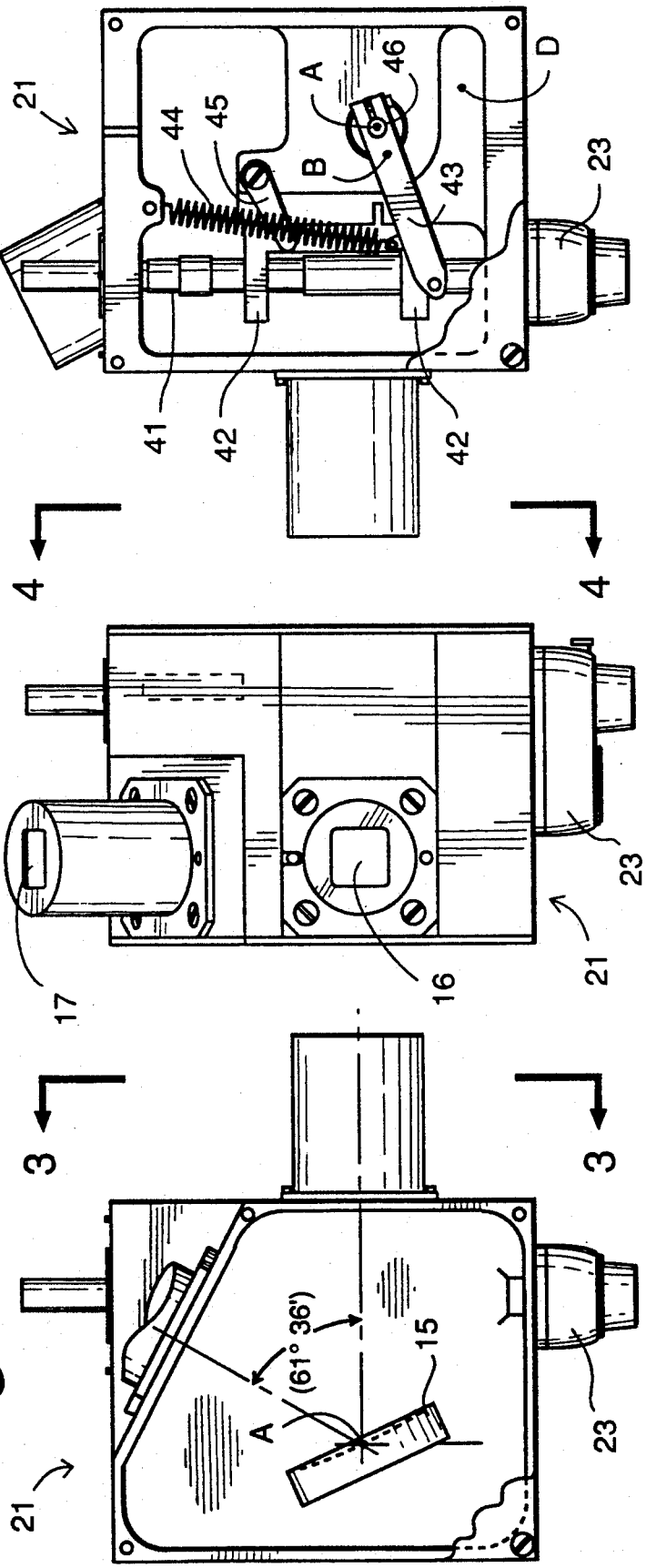

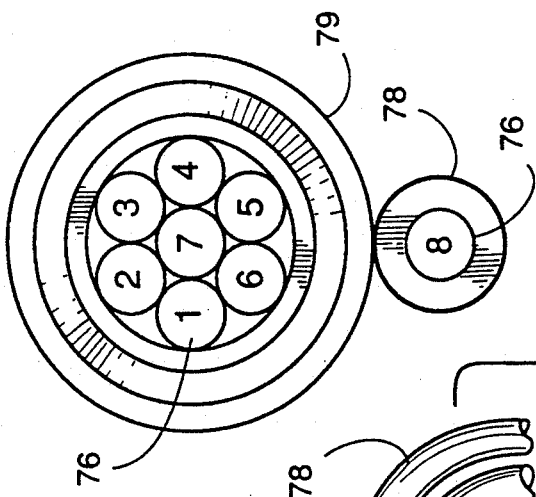
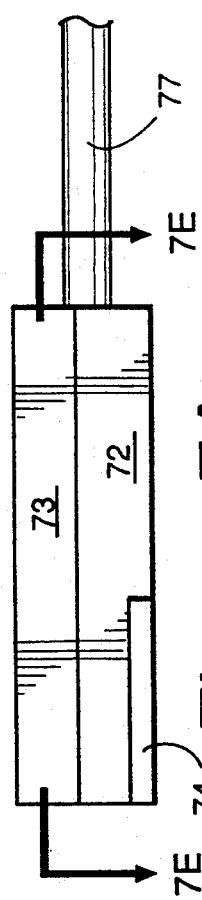
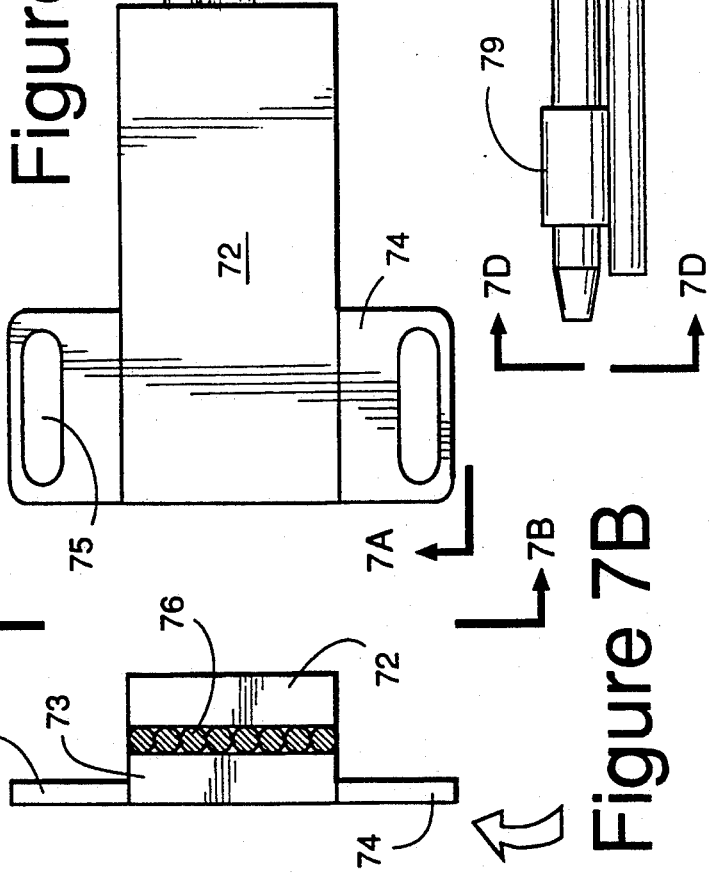
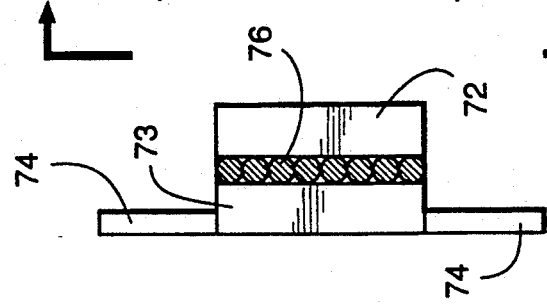

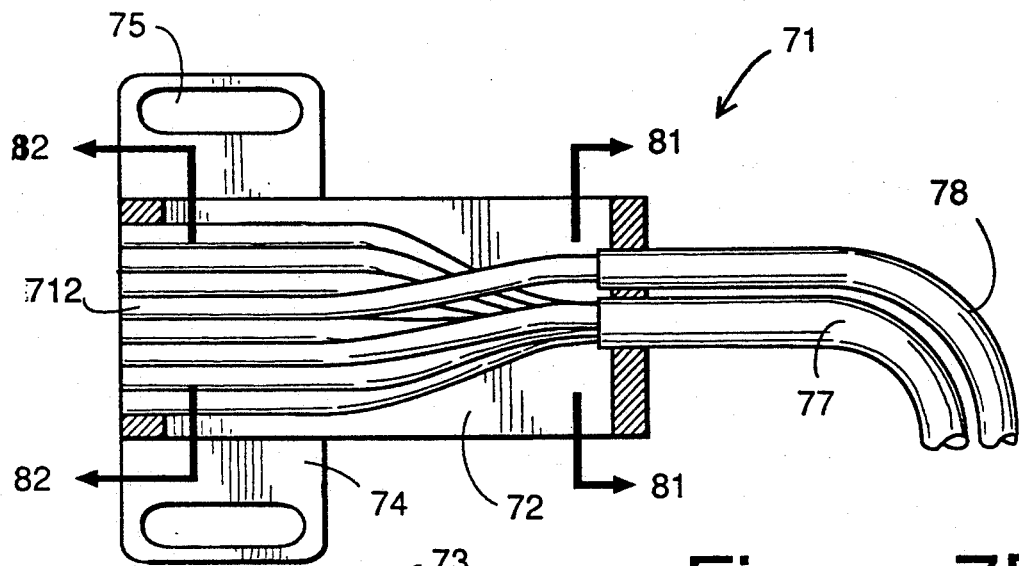
Figure 7E
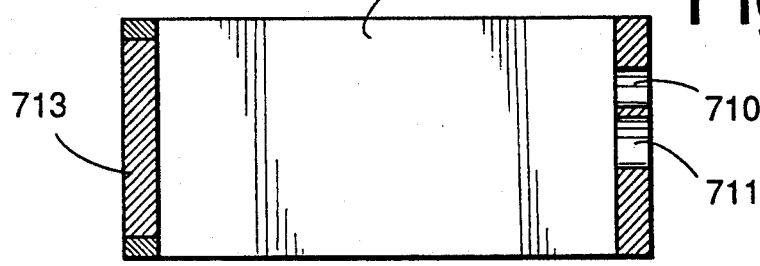
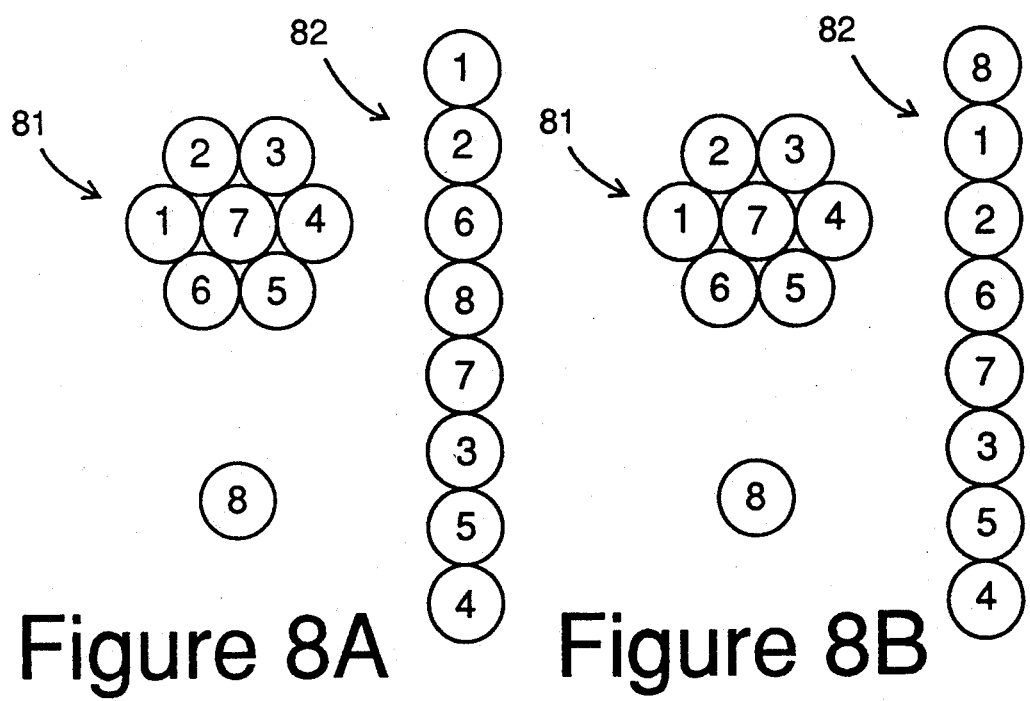
Figure 8A  Figure 8B

CALIBRATION TECHNIQUE FOR MONOCHROMATORS AND SPECTROPHOTOMETERS

BACKGROUND AND SUMMARY OF THE INVENTION

This invention relates in general to methods of calibrating photometers and relates more particularly to a calibration method of utilizing optical fibers to transmit light signals to the photometer. The word "photometer" herein means any device, such as monochromators, spectrophotometers and interference filters, that separates an input beam into spatially separated spectral components for measurement of a spectral distribution.

In the figures, each element indicated by a reference numeral will be indicated by the same reference numeral in every figure in which that element appears. The first two digits of any 4 digit reference numerals and the first digit of any two or three digit reference numerals indicates the first figure in which its associated element is presented.

Spectrophotometers, monochromators and dispersion optics packages are readily available from a number of sources and can be used as general purpose measuring instruments and can also be incorporated into other instruments for special applications. For example, in plasma processing of wafers, process endpoint detection can be recognized by use of a monochromator or a spectrophotometer to detect the endpoint of a wafer processing step.

It is becoming increasingly important to be able to accurately detect the endpoint of various steps in a wafer fabrication process. Submicron linewidths and ultrathin layer thickness are becoming common, especially in state of the art devices. In such devices, overprocessing can undercut features, thereby severely affecting yield.

Also, these state of the art devices require processing in single wafer systems. To maintain the same throughput as conventional batch wafer process systems, these single wafer systems must complete each process step much faster than was required in the batch process systems. It is therefore important for system throughput to be able to stop a process step as soon as it is completed. Although it was acceptable to run a batch wafer process system for a preselected interval, in single wafer systems it is important to be able to accurately detect the endpoint of a process step so that processing can be quickly terminated.

In virtually all dry etch processes, such as plasma etch, reactive ion etch (RIE), ion milling, reactive ion beam etch (RIBE), and magnetron etching, light is emitted from the gas phase reactants, from the gas phase products and/or from the film being etched. Etch endpoint occurs when the exposed portion of a film being etched has been etched to an interface between that film and an underlayer.

At etch endpoint, some product species cease to be produced and some reactant species cease to be consumed. Therefore, in the gas phase, the reactant species quickly increase in concentration and the product species quickly decrease in concentration. These changes produce concomitant changes in the associated emission and/or absorption spectra intensities of the gas phase and film. Various endpoint detectors are designed to detect this change in optical intensity. Similar changes occur in the optical output spectra of other types of wafer processing systems.

In the endpoint detection system of FIG. 1, light is passed through a fiber optic cable 10 from a wafer processing system, such as the Applied Materials PE5000 plasma chamber 11, to a spectral detector such as monochromator system 12. This system includes a monochromator 13 that is adjusted to direct onto a photomultiplier tube 14 light of a wavelength that changes in intensity when an etch process step reaches an underlayer interface. Light from plasma chamber 11 passes through fiber optic cable 10, through an entrance slit 16, diffracts off of grating 15 and a portion of the diffracted light passes through an exit slit 17 to the photomultiplier tube. A high voltage power supply applies to the photomultiplier tube a voltage that can be adjusted to vary the gain of the photomultiplier tube.

A motor is connected by a drive shaft to a radiation dispersive element such as concave holographic grating 15. This enables the dispersive element to be rotated to change the wavelength component that is directed onto the photomultiplier tube. An endpoint detection system is responsive to the output of the photomultiplier tube to extract in real time a portion of this output signal that is indicative of the endpoint of a process step. In an etch process, this endpoint detection system detects when the etch process reaches and clears a layer interface in the wafer, thereby defining the end-of-etch condition.

A spectrophotometer can be utilized in place of monochromator 13 and photomultiplier tube 14 to provide to the endpoint detection system a spectral output. In such a system, the endpoint detection system would extract from this spectral output the amplitude of the spectral distribution of the chemical species that is being monitored for endpoint detection. Such a system has the advantage of utilizing more than one frequency component of light, thereby, via mathematical analysis that utilizes the increased amount of data, improving the signal to noise ratio of the light from the chemical component being monitored.

Because the spectral distribution of the light from the plasma chamber typically exhibits a number of sharp peaks characteristic of the chemical species in the plasma chamber, it is important that the photometer be accurately calibrated to assure accurate detection of these peaks. The conventionally available photometer modules are typically calibrated at the factory. These modules also commonly include some mechanism for recognizing when the holographic grating is rotated to a preselected reference orientation referred to as the "home location".

For example, in the monochromator module from Instruments SA, Inc., the holographic grating is rotated in response to rotation of a lead screw. Attached to the lead screw is a mechanical counter that counts the number of revolutions of the lead screw. This counter provides a visual indication of the approximate rotation of the lead screw. A stepper motor is utilized to turn the lead screw a controlled number of steps. An electronic record of the number of times the motor was stepped provides an electronic indication of the rotational orientation of the holographic grating. There are 400 steps per revolution and one complete revolution corresponds to a wavelengh change of 100 nm for the light incident on the exit slit. Thus, each step corresponds to a 0.25 nm change in wavelength at the exit slit.

Unfortunately, various causes, including mechanical wear and slippage, can result in miscalibration of the photometer. Because accurate calibration is required for efficient and accurate wafer processing and because high quality processing is required for commercially acceptable chip throughput, it is important to assure that the photometer calibration is correct at all times. Therefore, a mechanism and method are needed that ensure accurate ongoing calibration of the photometer. It is known that SC Technology incorporates a mercury lamp source for calibration of its endpoint detection system, but no details of these calibration processes are known.

SUMMARY OF THE INVENTION

In accordance with the illustrated preferred embodiment, the model number 1061 monochromator module from Instruments SA, Inc. is modified to provide home sensing capability and self calibrating capability. The home sensing mechanism consists of a thin opaque element and a LED/photodetector element. The thin opaque element is attached directly to a sine arm used to rotate the holographic grating. When the grating is rotated to the home position, the opaque element interrupts the light from the LED to the photodetector, thereby producing an electrical indication that the grating is rotated to the home location.

Because the opaque element is attached directly to the sine arm, there are less sources of error in detecting the home position than in other systems such as in the above-mentioned Xinix, Inc. endpoint detection system in which the home location is detected by reflecting light off of the side of a lead screw nut. In that system, play between the lead screw and the lead screw nut can introduce error into detection of the home location. In addition, oxidation of the brass surface of the lead screw nut will vary the reflectivity, thereby further affecting the detection of the home location. The use of an opaque element attached directly to the sine arm eliminates these sources of error.

The calibration optical source is a tungsten filament mercury vapor lamp because it provides light having sharp peaks at 253.7 nm and 546.1 nm and can operate at much lower voltages than conventional mercury vapor lamps utilized in photometry. An optical fiber directs light from the calibration optical source to the entrance slit of the monochromator. A set of optical fibers direct light from the plasma chamber to this entrance slit. These fibers are arranged in a linear array so that light passes from them through the entrance slit. In an alternate embodiment, the entrance slit is eliminated and is replaced functionally by the linear array of exit ends of the optical fibers. This linear array can be curved slightly to compensate for some optical astigmatism inherent in this system of optical elements. At the linear array of optical fiber exit ends, the fiber(s) carrying the calibration signal are positioned at the middle of the linear array to ensure that miscalibration does not result from astigmatism.

During calibration, the plasma is turned off and the mercury lamp is turned on. The grating is rotated to the home location which is located just outside of the useful optical range of the photometer. A stepper motor rotates the grating until the wavelength of light directed onto the exit slit is adjacent to a first calibration peak and then scans across the first peak, executing a set of measurements across the peak and storing the data in memory. The grating is then rotated back to the last detected maximum value measured within this peak. The Automatic Gain Control and the sensitivity of the photodetector are adjusted to optimize the accuracy of measurement of this peak. This peak is again scanned and peak center is defined to occur at the midpoint between the 50% power points of this peak. The wavelength of this peak is defined to be the known wavelength of this calibration peak (i.e., 253.7 nm). The grating is then rotated until the wavelength of light directed to the exit slit is adjacent to the next calibration peak and these steps of locating peak center are repeated. The measured wavelength, in nanometers, is equal to $253.7 + 0.25 \cdot N$, where N is the number of steps between the two peaks. If the difference between the measured wavelength of this peak and its known wavelength is more than twice the specified accuracy of the photometer, then an error condition is signalled to the user to indicate that a repairman should be called.

These and other objectives and advantages of the present invention will become clear from the detailed description given below in which a preferred embodiment is described in relation to the drawings. The detailed description is presented to illustrate the present invention, but is not intended to limit it.

DESCRIPTION OF THE FIGURES

FIGS. 2–4 illustrate three views of a preferred embodiment of a monochromator suitable for use in the wafer processing endpoint detection system of FIG. 1.

FIG. 5 illustrates a thin opaque flag utilized as part of a home location detection system.

FIG. 6 illustrates a home location sensor that, in cooperation with the flag of FIG. 5, detects the home location.

FIGS. 7A–7C are three views of a fitting that takes a set of 7 optical fibers from a source under test and an optical fiber from a calibration source and aligns the output ends of these fibers into a linear array for input to a monochromator.

FIG. 7D is an end view of an optical cable coupler, illustrating the arrangement of 7 optical fibers within such coupler.

FIG. 7E is a cross-sectional view of the fitting of FIG. 7A, illustrating the rearrangement of the fibers from the circular array structure within the optical cable to the linear array structure within the fitting.

FIGS. 8A and 8B are schematics of the arrangement of optical fibers at the entrance slit and within a fiber optic cable.

DESCRIPTION OF THE PREFERRED EMBODIMENT

Figure 1:
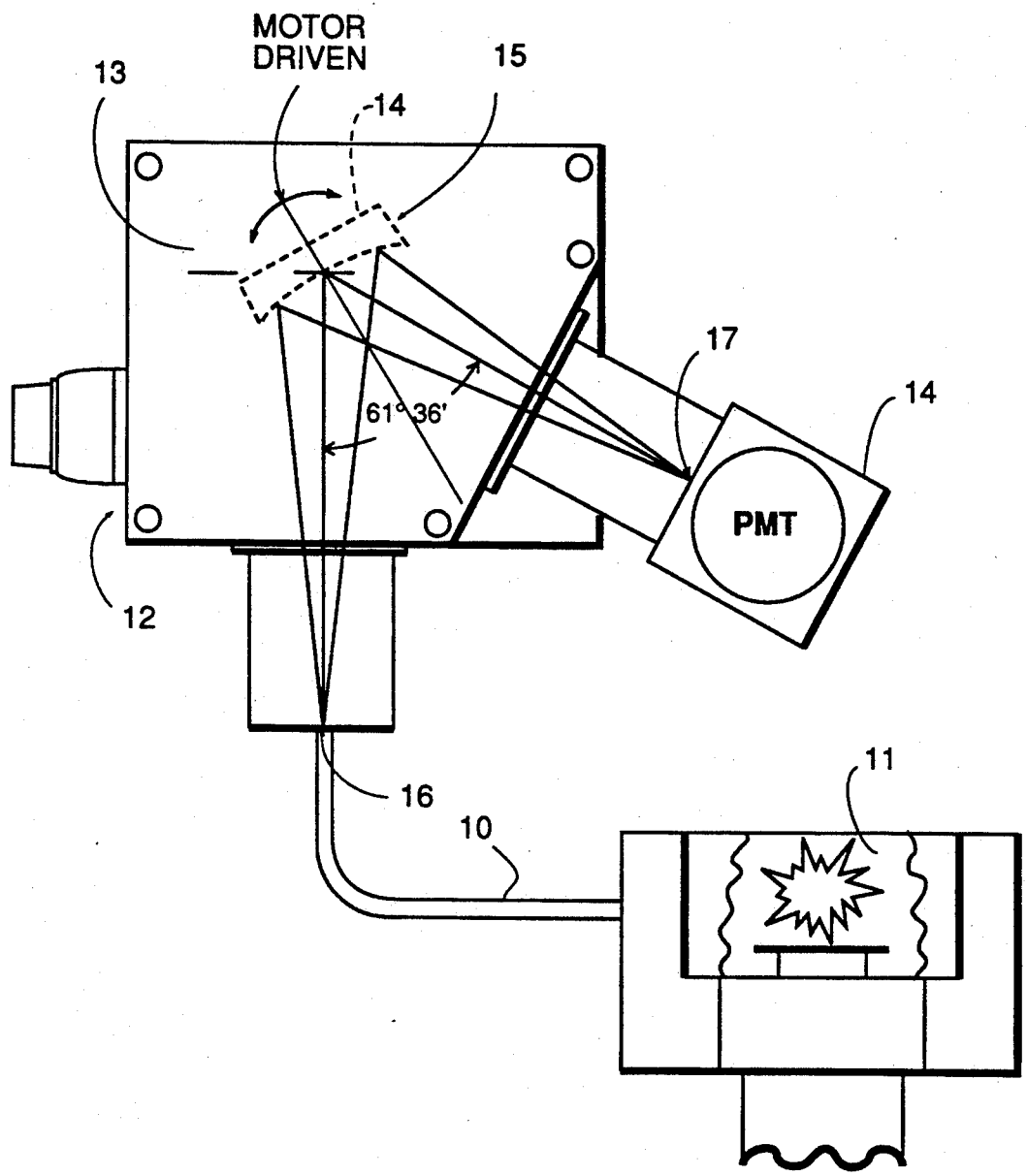
FIG. 1 illustrates the use of a monochromator to measure the intensity of selected wavelengths of light from a plasma reactor chamber for process endpoint detection.

FIGS. 2–4 illustrate three views of a preferred embodiment of a monochromator suitable for use in the wafer processing endpoint detection system of FIG. 1. This monochromator is a modified version of a model 1061 monochromator 21 available from Instruments SA, Inc. Light is carried from a plasma processing chamber through a set of optical fibers and through an entrance slit 16 onto a curved holographic grating 15.

Grating 15 is rotatable about an axis A (shown in FIGS. 2 and 4) to control the wavelength of light that is diffracted onto an exit slit 17.

The angular orientation of grating 15 about axis A is varied by rotation of a lead screw 41. Grating 15 and a sine arm 43 are both coupled to a shaft 46 that is centered on axis A. The sine arm is rotatably biased to a lead screw nut 42 that is threaded onto the lead screw. A spring 44 biases the lead screw nut and sine arm against the lead screw to eliminate play between the threads of this nut and arm relative to the screw. A leaf spring 45 biases nut 42 against a shoulder to prevent rotation of nut 42 around the axis of screw 41. When the lead screw is rotated, the lead screw nut moves along the lead screw, thereby rotating the sine arm and the grating about axis A.

The monochromator from Instruments SA, Inc. is modified by the addition of a thin opaque piece of material, referred to herein as a "flag" 51 (illustrated in FIG. 5), and a home sensor 61. Flag 51 is mounted to the sine arm at point B such that the surface of the flag is perpendicular to axis A. Home sensor 61 (illustrated in FIG. 6) contains a light emitting diode (LED) 63 and a photodiode 64 and is mounted to monochromator 21 at a point D such that the flag can pass through a gap 62 between the LED 63 and the photodiode 64. Position D is such that, as the grating is rotated to the home location, the flag interrupts the beam of light from the LED to the photodiode, thereby producing an electrical indication that the home location has been reached.

Grating 15 can rotate through an angle sufficient to direct onto the exit slit light of wavelength λ within the range 140-999 nm. However, the photomultiplier tube and other optical components are such that significantly flat spectral measurement is obtained over the more limited range from 200-800 nm. Position D at which the home sensor 61 is mounted is chosen so that, at the home location, the light directed onto the exit slit is within the range 177±30 nm.

Lead screw 41 can be turned by hand by means of a knob 23 and can also be turned by a stepper motor (not shown). Lead screw 41 is also attached to a mechanical counter that displays the approximate wavelength (in nm) being monitored.

In order to calibrate the monochromator, an optical fiber is positioned to carry light from a reference light source to the entrance slit of the monochromator. A mercury vapor light source is commonly used because it provides narrow, intense peaks within the 200-800 nm range commonly used for spectrometry. As long as the wavelength of light incident onto the entrance slit varies substantially linearly with angular rotation of the holographic grating about axis A, only two points are needed to fully calibrate the monochromator. Unfortunately, the mercury arc lamps typically utilized in monochromators require a voltage on the order of 800 volts to initiate discharge and then require a voltage on the order of 270 volts to maintain operation. For cost and safety reasons, it is always advantageous to operate at lower voltages. Therefore, the lamp selected to provide the calibration light beam is a tungsten filament, mercury vapor lamp such as the G4S11 Germicidal lamp available from General Electric Company for use in producing a sterile environment.

FIGS. 7A-7E illustrate a fitting 71 that aligns into a linear array the exit ends of a set of optical fibers 76 consisting of an optical fiber carrying a calibration signal and a set of optical fibers carrying a measurement signal. Because light is injected into the monochromator through entrance slit 16, fitting 71 is needed to align the optical fibers into a linear array of width and length comparable to the width and length of entrance slit 16. Fitting 71 is intentionally spaced from the entrance slit by a distance equal to a few times (on the order of seven times) the diameter of the smallest diameter optical fiber in cable 77 so that precise alignment of the exit ends of the fibers with the entrance slit is not required. This allows the light to spread out before striking the entrance slit, thereby enabling only rough alignment between this fitting and slit to still assure that the entrance slit is illuminated. This spreading of the light reduces sensitivity somewhat, but makes the system much more manufacturable and much less sensitive to subsequent misalignment occurring during use.

In alternate embodiments, entrance exit-slit 16 can be eliminated because the linear array of exit ends of the fibers performs the slit function of producing a narrow oblong source of light for the monochromator. In such an embodiment, the linear array of exit ends can be in the shape of an arc selected to compensate for astigmatism in the monochromator.

FIGS. 7A-7C are side, top and end views, respectively, of this fitting. Fitting 71 consists of a lower shell 72, an upper shell 73 and a pair of mounting tabs 74 in each of which is formed a bolt hole 75. An optical cable 77 carrying a set of 7 optical fibers and an optical cable 78 carrying a single optical fiber are attached to fitting 71 at a first end. Within the fitting, these optical fibers are spread out into a linear pattern as illustrated in FIG. 7B. Light from a reference source, such as a tungsten filament mercury vapor lamp, is carried through optical cable 78 to fitting 71. Light from a source being measured, such as plasma chamber 11, is carried through optical cable 77 to fitting 71.

A coupler 79 is attached to an end of optical cable 77 to enable the cable length to be extended as needed. Coupler 79 can also be used as a feedthrough to connect the fiber through a bulkhead. FIG. 7D is an end view of cable 78 and coupler 79, illustrating the arrangement of the 7 optical fibers within cable 77 and coupler 79. This figure illustrates that seven fibers is a convenient number because these seven fibers pack into the close-packed structure familiar from hexagonally symmetric crystals. Other numbers of cables that pack into close-packed, substantially cylindrical cables are 19 and 37 fibers.

Figure 9:
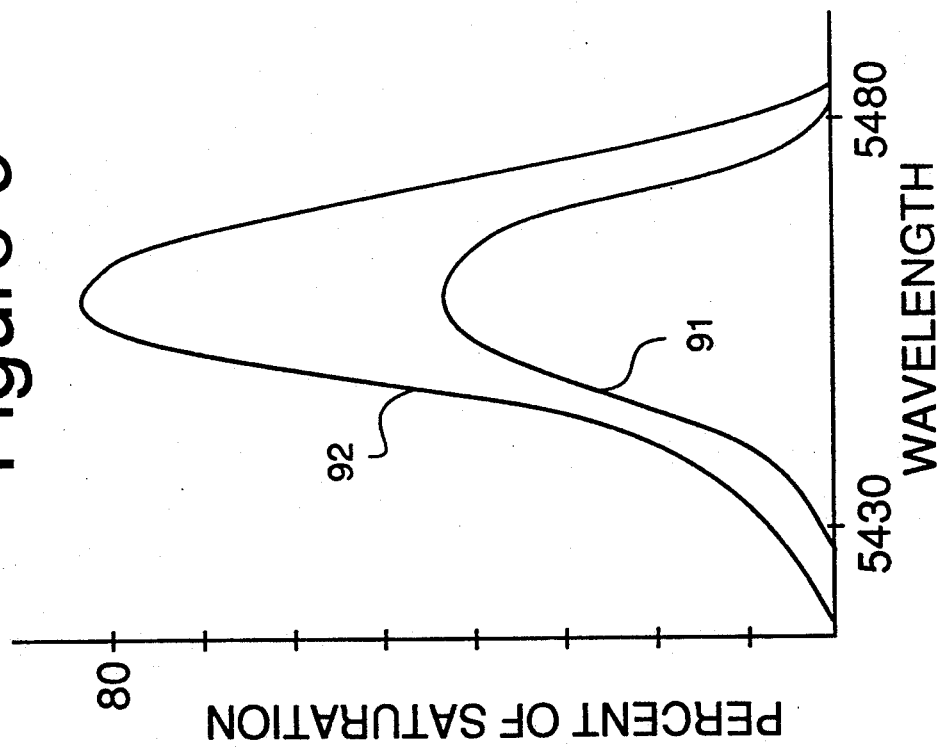

Grating 15 has sufficient astigmatism that it is important to direct calibration light onto the center of the entrance slit. FIG. 9 illustrates the shapes and locations of a detected peak 91 for light transmitted through the fiber in calibration cable 78 and a detected peak 92 for light transmitted through the fibers in cable 77. In this figure, the exit end of the fiber from calibration cable 78 is substantially at the center of the linear array of exit ends of the fibers. Because the exit end of the optical fiber carrying the calibration signal is substantially at the center of the entrance slit of the monochromator, peaks 91 and 92 are substantially symmetric and have substantial alignment of the centers of these peaks.

An arrangement of the exit ends of the optical fibers that achieves this is illustrated in FIG. 8A. FIG. 7E is a cross-sectional view of the fitting of FIG. 7A, illustrating the rearrangement of the fibers from the circular array structure within the optical cable to the linear array structure within the fitting. Cluster 81 illustrates the pattern of the fibers as they exit from cable 77 into fitting 71. Cluster 82 illustrates the linear alignment of fibers at the exit end of fitting 71. Fiber 8, carrying the calibration signal, is located at the 4th position from the top of the linear array 82 of exit ends. An equally good choice would have been to locate this fiber at the 4th position from the bottom of linear array 82.

Figure 10:
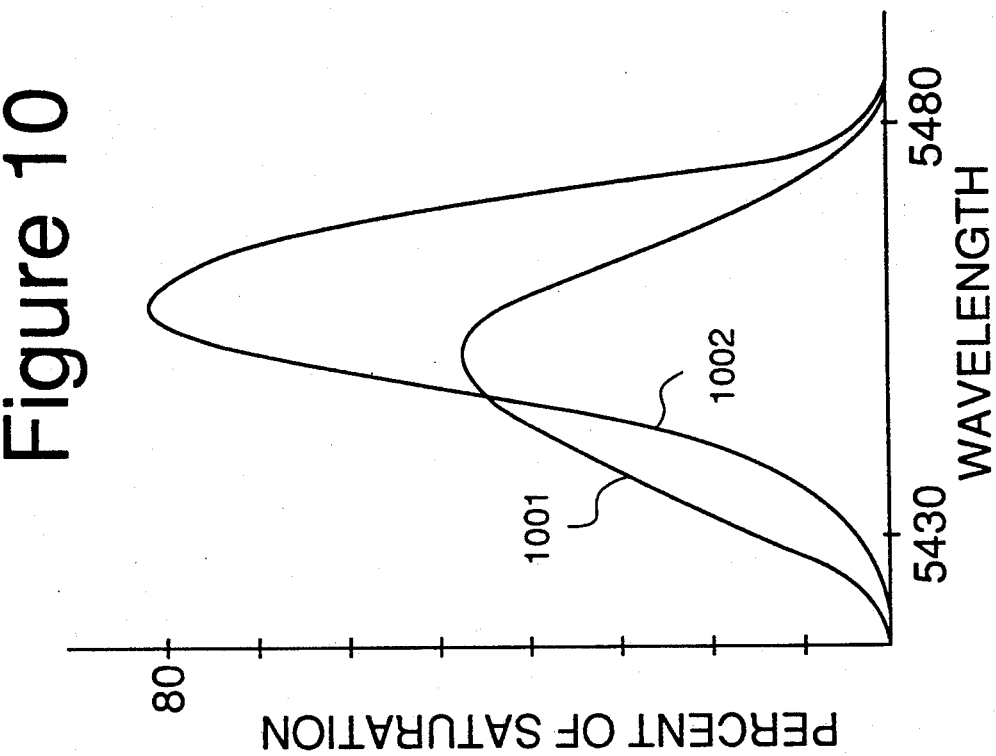
FIGS. 9 and 10 illustrate the calibration error that results if the optical fiber for transmission of calibration light has its exit end away from the optical center of the entrance slit of the monochromator.

FIG. 10 illustrates the shapes and locations of a detected peak 1001 for light transmitted only through the fiber in calibration cable 78 and a detected peak 1002 for light transmitted only through the fibers in cable 77. In this figure, the exit end of the fiber from calibration cable 78 is at the end of the linear array of exit ends of the fibers. Such an alignment is illustrated in FIG. 8B. As can be seen in this figure, these peaks are much less symmetric than the peaks of FIG. 9 and the centers of these peaks are offset. This offset between peaks for light of the same wavelength, but transmitted through different fibers means that an equal error will occur in measurements of sample light transmitted through cable 77. This error is likely to be even larger near the 800 nm upper limit of the optical range than it is at the wavelengths of FIG. 10.

If the astigmatism is sufficiently extreme, optimal alignment of peak 1001 with peak 1002 may not occur when the exit end of the calibration fiber is located at the physical center of the entrance slit. By the "optical center of the entrance slit" is meant that, when the calibration fiber is positioned at that location, then the astigmatic misalignment of peaks 91 and 92 is minimized over the range of operation of the monochromator. Similarly, in embodiments in which more than one optical fiber is utilized to carry the calibration signal, it may be advantageous, depending on the astigmatism of the system, to align the exit ends of these fibers at locations that are not even physically adjacent, but that minimize the astigmatic effects on calibration and measurement.

Figure 11:
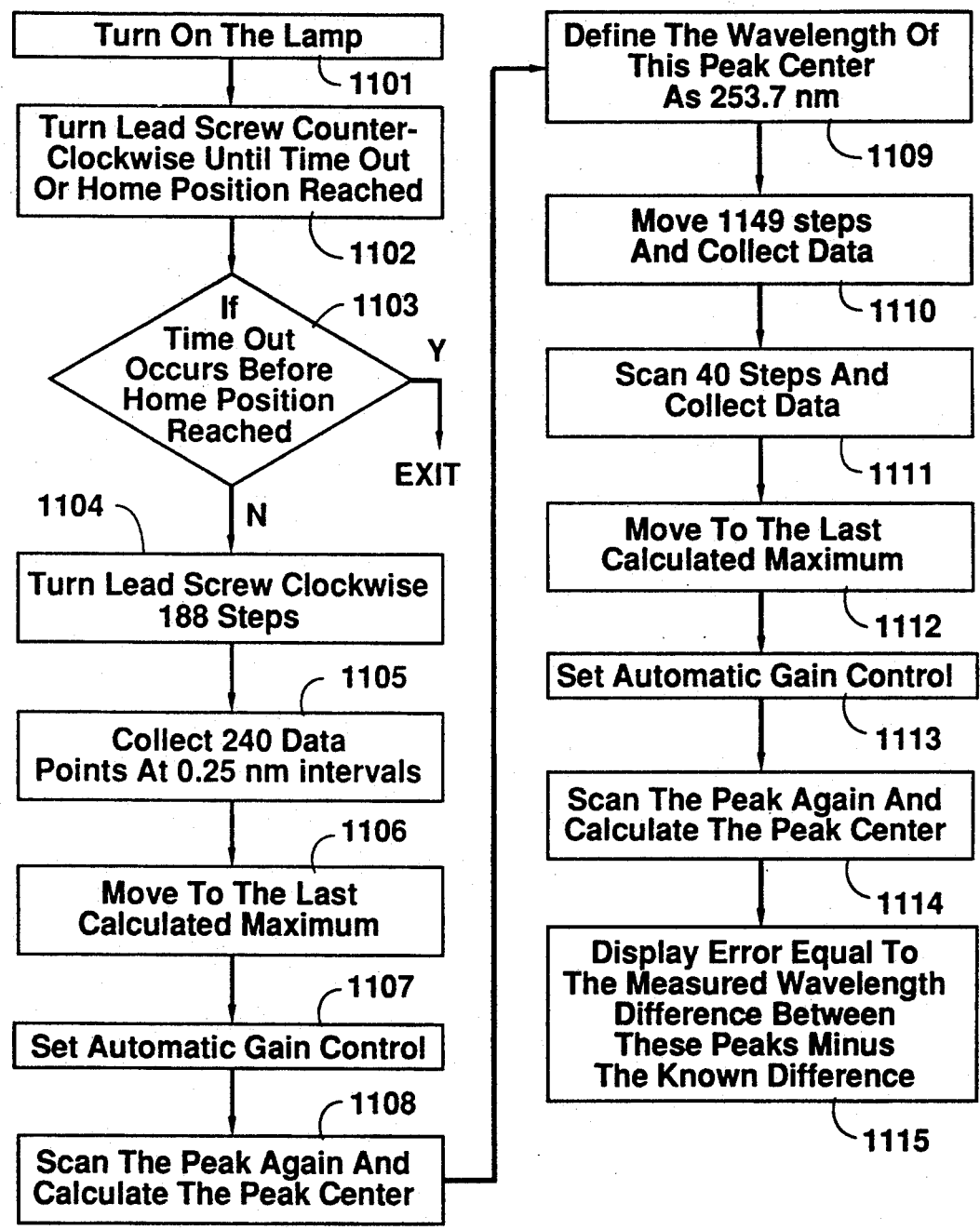
FIG. 11 is a flow diagram of the calibration and measurement process.

The process of calibration and measurement is outlined as steps 1101-1115 in FIG. 11. The calibration lamp is turned on and allowed to warm up (step 1101). With the plasma off in the plasma chamber, the diffraction grating is rotated either until home sensor 61 indicates that the home position at approximately 170 nm has been reached or until some preset timeout period has been reached, in which latter case an indication is produced that the monochromator could not reach the home position (step 1102). If the home position is reached (step 1103), then the lead screw is turned clockwise 188 steps to select a detected wavelength of substantially 224 nm (step 1104). The calibration peak at 253.7 nm is scanned by repeatedly stepping the motor and measuring the light intensity at each of 240 successive steps to produce a set of measurements at approximately 0.25 nm intervals from 224 nm to 284 nm (step 1105). The grating is rotated to the last maximum within this measurement span. That is, if the maximum value of intensity is detected at more than one point in this interval, then the wavelength is stepped to the last of these maxima (1106). An automatic gain control (AGC) is activated to adjust the gain of the photomuliplier tube to 70% of the saturation level of the photomultiplier tube (step 1107).

The wavelength is reduced by 5 nm and this peak is scanned again at this adjusted gain level. This scan is extended from 5 nm below the peak to 5 nm above the peak and measurements are made at each step of this scan. This new data is then processed to determine the midpoint between the two 50% power point of the peak (step 1108). The wavelength of this point is defined as being 253.7 nm, which is the wavelength of the mercury vapor lamp peak at this point (step 1109).

The motor is rotated through 1149 steps to select a wavelength substantially at 541.1 nm, which is approximately 5 nm below the next calibration peak of the mercury vapor lamp (step 1110). Measurements are made at each of 40 successive steps of the motor to scan this calibration peak (step 1111) and then stepped back to the last calculated maximum (step 1112). The AGC is again adjusted to 70% of saturation (step 1113) and the peak is again scanned. The peak is defined to occur at the midpoint between the 50% power points of this peak (step 1114). An error indication is generated (step 1115) equal to the difference between the actual step count between the first and second peaks and the expected step count between the peaks (i.e., the error indication is equal to the actual step count travelled between the first and second calibration peaks minus (546.1−253.7)·4. If this error exceeds some preselected value (e.g., 8 steps, which corresponds to twice the typical ±1 nm accuracy of typical monochromators), then an indication is presented to the user that a service operator should be called to calibrate the monochromator.

We claim:
1. An optical test apparatus comprising:
a photometer having an optical entrance for input of an optical signal;
at least one optical fiber having an exit end at said optical entrance for transmission of sample light to the photometer optical entrance;
at least one optical fiber having an exit end at said optical entrance for transmission of calibration light to the photometer optical entrance; and
means for aligning said exit ends of all of these optical fibers into a linear array
wherein at least one optical fiber is utilized to carry light from a calibration source to said optical entrance, said at least one optical fiber for carrying calibration light is positioned at the optical entrance in such a way that, over a wavelength range of the test apparatus, minimizes astigmatic misalignment of a pair of peaks, a first of these peaks being produced in response to light of wavelength λ transmitted only through said at least one calibration fiber and the other of these two peaks being produced in response to light of wavelength λ transmitted only through said at least one fiber for transmission of sample light.

2. An optical test apparatus as in claim 1 wherein said calibration light has at least 2 peaks, said apparatus further comprising:
means, utilizing these two peaks, for calibrating wavelength measurement accuracy of this apparatus.

3. An optical test apparatus as in claim 1 wherein said at least one optical fiber for transmission of calibration light has its exit end substantially in the optical center of said linear array.

4. An optical test apparatus comprising:
a photometer having an optical entrance for input of an optical signal;
at least one optical fiber having an exit end at said optical entrance for transmission of sample light to the photometer optical entrance;
at least one optical fiber having an exit end at said optical entrance for transmission of calibration light to the photometer optical entrance;

means for aligning said exit ends of all of these optical fibers into a linear array; and an entrance slit between said optical fibers and said optical entrance of the photometer, wherein the exit ends of the optical fibers are spaced from the entrance slit by a few times a smallest diameter of these optical fibers.

5. An optical test apparatus as in claim 4 wherein each of said optical fibers has a diameter substantially equal to a width of an entrance slit at the optical entrance of the photometer.

6. An optical test apparatus comprising:

a photometer having an optical entrance for input of an optical signal;

at least one optical fiber having an exit end at said optical entrance for transmission of sample light to the photometer optical entrance;

at least one optical fiber having an exit end at said optical entrance for transmission of calibration light to the photometer optical entrance;

means for aligning said exit ends of all of these optical fibers into a linear array; and a tungsten filament mercury vapor lamp as a source of calibration light, whereby only low voltage levels are required for the calibration light source.

* * * * *